United States Patent [19]

Kathawala

[11] 4,233,292
[45] Nov. 11, 1980

[54] CYCLOPROPYL SULFONIUM SALTS

[75] Inventor: Faizulla G. Kathawala, West Orange, N.J.

[73] Assignee: Sandoz, Inc., E. Hanover, N.J.

[21] Appl. No.: 10,016

[22] Filed: Feb. 7, 1979

[51] Int. Cl.³ .................. A61K 31/69; A61K 31/095; C07C 147/00
[52] U.S. Cl. .................. 424/185; 424/335; 568/18
[58] Field of Search .......................... 424/185, 335; 260/607 B

[56] References Cited

U.S. PATENT DOCUMENTS

| | | |
|---|---|---|
| 2,193,963 | 3/1940 | Harris .................. 260/607 B |
| 3,534,105 | 10/1970 | Distler et al. .......... 260/607 B |
| 3,873,488 | 3/1975 | Gibbs et al. ........... 260/607 B |

Primary Examiner—Frederick E. Waddell
Attorney, Agent, or Firm—Gerald D. Sharkin; Richard E. Vila; Frederick H. Weinfeldt

[57] ABSTRACT

Cyclopropyl alkyl arylsulfonium salts, e.g., cyclopropyl n-propyl phenylsulfonium tetrafluoroborate, are useful as pharmaceutical agents.

3 Claims, No Drawings

CYCLOPROPYL SULFONIUM SALTS

This invention relates to sulfonium salts and more particularly to cyclopropyl alkyl arylsulfonium salts, as well as to pharmaceutical compositions containing such compounds, and to the pharmaceutical use of such compounds.

Compounds of this invention may conveniently be represented by the formula I:

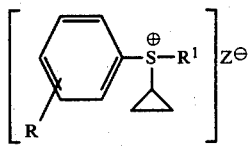   I.

wherein
R is a hydrogen atom, alkyl, having from 1 to 4 carbon atoms, e.g., methyl, alkoxy, having from 1 to 4 carbon atoms, e.g., methoxy, halo having an atomic weight of from about 18 to 36, i.e., fluoro or chloro, and trifluoromethyl;
$R^1$ is alkyl having from 1 to 20 carbon atoms; which may be branched or unbranched, but is preferably unbranched, e.g., n-propyl, n-octyl, n-tetradecyl, or octadecyl; hence lower alkyl (1 to 7 carbons) or higher alkyl (8 to 20 carbons); and
Z is a complex anion which is a member of the group consisting of $BF_4$; $ClO_4$; and $SO_3$—$R^2$,
wherein $R^2$ is methyl, phenyl, p-tolyl, or 2-naphthyl*
*the 2-naphthyl radical is also known as β-naphthyl Compounds I may conveniently be prepared by reacting (process a) a suitable aryl, cyclopropylsulfide of the formula II:

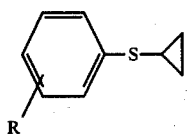   II.

in which R is as defined above, with a haloalkyl of the formula III:

X-$R^1$   III.

in which
$R^1$ is as defined above; and
X is halo having an atomic weight of from about 79 to 127, i.e., bromo or iodo, preferably iodo, in the presence of a silver salt having the formula IV:

Ag-Z   IV.

in which Z is as defined above.

(Process a) is conveniently carried out at moderate temperatures, e.g., from about 15° to 40° C., preferably at room temperature, in an inert solvent, e.g., nitromethane, under essentially anhydrous conditions. The silver salt (IV) should be present in an amount of at least one equivalent, based on the weight of the compound II employed, as it provides the Z-portion of the reaction product (I).

Compounds I in which Z is other than $BF_4$, i.e., compounds I′:

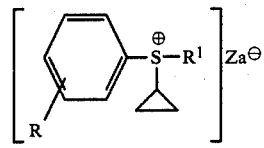   I′ in which R, and $R^1$ are as defined above, and $Z_a$ is the same as Z, as defined above when it is other than $BF_4$, may be prepared from corresponding compounds I in which Z is $BF_4$, i.e., compounds I″:

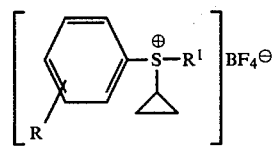   II″ in which R, and $R^1$ are as defined above, by an exchange reaction (process b), by heating a Compound I″ in the presence of an acid of the formula V:

H-$Z_a$,   V.

in which $Z_a$ is as defined above; at a temperature of about 65° to 120° C.; thus it yields an anion suitable as Z, which is other than $BF_4$.

A compound I′ in which Z is $ClO_4$ (i.e., a compound I‴ is preferably prepared by heating a compound I″ in the presence of an excess of $HClO_4$ in water, at from about 70° to 85° C.; it being particularly convenient to heat on a steam bath.

A compound I′ in which Z is a sulfonate-type anion of the formula $SO_3$—$R^2$, i.e., a compound $I^{iv}$, is preferably prepared by heating a compound I″ with an excess of the corresponding acid form, i.e. a reagent of the formula $HSO_3$—$R^2$, ($R^2$ being as defined above) in the presence of water, at from about 85° to 100° C.; e.g., at reflux temperature of the reaction mixture.

It is also convenient to add a small amount of sodium or potassium hydroxide, e.g., as an aqueous solution, such as 2N, to the compound I″ reactant in water, when such is difficultly soluble in water.

The products of the above-described reactions may be recovered and refined in conventional manner, e.g., by crystallization, distillation or chromatographic techniques, such as eluting from a chromotographic column or separating on a silica layer.

Starting materials and reagents used in the above-described reactions, e.g., compounds II, III, IV and V are either known and obtained by methods described in the literature, or where not known, may be obtained by methods analogous to those described in the literature. Some of the reactants and starting materials are commercially available.

The above-described reactions may conveniently be represented by the following reaction scheme wherein R, $R^1$, and $Z_a$ are as defined above:

REACTION SCHEME

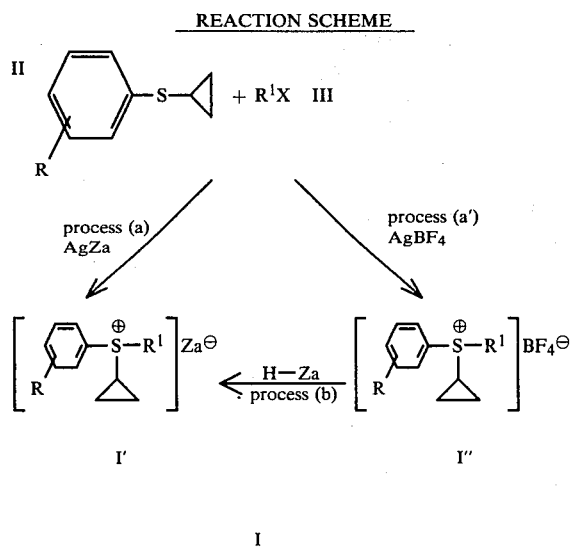

I

STATEMENT OF UTILITY

The compounds of formula I are useful because they possess pharmacological activity in animals, particulary as anti-obesity agents in mammals as indicated by the glucose transport test carried out in Male Wistar rats dosed orally with from about 2 to 200 mg/kg of active material, after at least 20 hours of fasting. One hour after receiving the drug, the animal is sacrificed and the upper small intestine is removed and washed with glucose-saline. A 5 cm section of the intestine is everted so that the mucosal surface is on the outside. One end of the segment is tied off and the center of the sac so formed, is filled with oxygen saturated Kreb's bicarbonate buffer. The other end is then closed to form a sac and the sac is incubated in 10 ml. of oxygen saturated bicarbonate buffer for 60 minutes at 37° C. Both the outside and inside solutions contain initially 0.3% of glucose. At the end of the incubation time the glucose content of the outer (mucosal) and the inner (serosal) solution is determined using the standard Autoanalyzer procedure. Similar procedures are prepared simultaneously from animals receiving the vehicle only to serve as controls. The percent inhibition of glucose transport caused by the drug is calculated by the formula $$\% I = 100 - \left( \frac{St - Mt}{Sc - Mc} \times 100 \right)$$

where
I equals inhibition
S equals glucose concentration (mg%) of serosal fluid at the end of the experiment
M equals glucose concentration (mg%) of mucosal fluid at the end of an experiment
c equals control animal
t equals drug treated animal.

For such usage, the compounds (I) may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example from about 20 to 50% of ethanol, and the like, or parenterally in the form of sterile injectable solutions or suspensions containing from about 0.5 to 5% suspending agent in an isotonic medium. These pharmaceutical preparations may contain, for example, from 0.5% up to about 90% of the active ingredient in combination with the carrier, more usually between 5% and 60% by weight.

The effective dosage of active ingredient employed for the treatment of obesity may vary depending on the particular compound employed, the mode of administration and the severity of the condition being treated. However, in general, satisfactory results are obtained when the compounds of formula I are administered at a daily dosage of from about one milligram to about 50 milligrams per kilogram of animal body weight. Administration daily may be as a single dose, e.g., in sustained release form, or in divided doses, e.g., two to four times a day to obtain the desired level of administration. For most large mammals, the total daily dosage is from about 50 milligrams to about 3000 milligrams. Dosage forms suitable for internal use comprise from about 10 to about 1500 milligrams of the active ingredient in intimate admixture with a solid or liquid pharmaceutically acceptable carrier. Solid carriers include starch, lactose, calcium carbonate and kaolin, while liquid carriers include sterile water, polyethylene glycols and edible oils such as corn, peanut and sesame oils, as are appropriate to the nature of the active ingredient and the particular form of administration desired.

Oral administration is preferred. The preferred pharmaceutical compositions from the stand-point of ease of preparation and administration are solid compositions, particularly tablets and hard-filled capsules.

The following examples are illustrative of the invention. In the examples all temperatures are centigrade and room temperature is 20° to 35° C., unless indicated otherwise.

EXAMPLE 1.

Preparation of cyclopropyl n-propyl phenyl-sulfonium tetrafluoroborate.

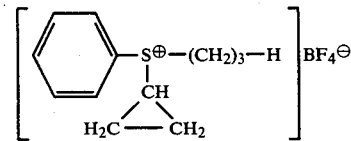

To a solution of 7.7 g. cyclopropyl phenyl sulfide and 9.4 g. n-propyl iodide in 100 ml. nitromethane is added in one portion 10.0 g. silvertetrafluoroborate. The reaction mixture is stirred at room temperature for 18 hours. Thereafter 100 ml. of methylene chloride is added, the reaction mixture filtered to remove precipated silveriodide and the filtrate evaporated i.v., to dryness. From the residue is crystallized from ethanol, the title product; m.p. 67°-70°.

Repeating the procedure of this example, but using in place of the n-propyl iodide, an approximately equivalent amount of
(a) n-octyl iodide;
(b) n-decyl iodide;
(c) n-tetradecyl iodide;
(d) n-octadecyl iodide; or (e) n-propyl bromide;
(f) methyl iodide;
there is accordingly obtained:
(a) cyclopropyl n-octyl phenylsulfonium tetrafluoroborate (as an oil);
(b) cyclopropyl n-decyl phenylsulfonium tetrafluoroborate;
(c) cyclopropyl phenyl n-tetradecylsulfonium tetrafluoroborate (waxy solid);
(d) cyclopropyl n-octadecyl phenylsulfonium tetrafluoroborate (m.p. 50°–52°);
(e) cyclopropyl n-propyl phenylsulfonium tetrafluoroborate; and
(f) cyclopropyl methyl phenylsulfonium tetrafluoroborate (as an oil).

EXAMPLE 2

Cyclopropyl n-propyl phenylsulfonium perchlorate 5.0 g cyclopropyl n-propyl phenylsulfonium tetrafluoroborate is dissolved in 50 ml distilled water by heating on a steam bath. To the resulting solution is then added 15 ml of 48% perchloric acid. The solution is then cooled and the percipitate which results filtered, washed with water, and dried under vacuum to give cyclopropyl n-propyl phenylsulfonium perchlorate.

Repeating the general procedure of this example using appropriate starting materials there is likewise prepared
(a) cyclopropyl n-decyl phenylsulfonium perchlorate; and
(b) cyclopropyl n-octadecyl phenylsulfonium perchlorate.

EXAMPLE 3

Cyclopropyl n-propyl phenylsulfonium p-Toluenesulfonate

To a solution of 12.0 g cyclopropyl, n-propyl phenylsulfonium tetrafluoroborate in 200 ml distilled water at 100°, is added gradually a solution of 60.0 g para-toluenesulfonic acid in 200 ml distilled water. The resulting mixture is cooled and extracted several times with methylene chloride. The combined methylene chloride extracts, after washing with water, are dried over anhydrous sodium sulfate, filtered and evaporated in vacuo to dryness to obtain a residue. From the residue is crystallized from ethanol, the unreacted cyclopropyl n-propyl phenyl sulfonium tetrafluoroborate which is separated by filtering, and the mother liquor evaporated to dryness to obtain a residue. The residue thereby obtained is treated again as above with lesser amounts of ethanol until all the unreacted starting material is removed, to leave behind refined cyclopropyl n-propyl phenylsulfonium p-toluene sulfonate (as an oil).

Repeating the procedure of this example, but using in place of the p-toluenesulfonic acid, an equivalent amount of methylsulfonic acid, benzene sulfonic acid or 2-naphthalene sulfonic acid, there is accordingly obtained cyclopropyl n-propyl phenylsulfonium methylsulfonate; cyclopropyl n-propyl phenylsulfonium phenylsulfonate; and cyclopropyl n-propyl phenylsulfonium 2-naphthylsulfonate (amorphous solid) respectively.

EXAMPLE 4

Repeating the procedure of Example 1, but using in place of the cyclopropyl phenylsulfide used therein, an approximately equivalent amount of:
(a) cyclopropyl p-tolylsulfide;
(b) cyclopropyl p-methoxyphenylsulfide;
(c) p-chlorophenyl cyclopropylsulfide; or
(d) cyclopropyl m-trifluoromethylphenylsulfide; there is accordingly obtained:
(a) cyclopropyl n-propyl p-tolylsulfonium tetrafluoroborate (as an oil);
(b) cyclopropyl p-methoxyphenyl n-propylsulfonium tetrafluoroborate (as an oil);
(c) p-chlorophenyl cyclopropyl n-propylsulfonium tetrafluoroborate and
(d) cyclopropyl n-propyl m-trifluoromethylphenylsulfonium tetrafluoroborate (as an oil).

EXAMPLE 5

Repeating the procedures of Examples 1, 3 and 4 using appropriate reactants, there is accordingly obtained:
(a) cyclopropyl n-octyl phenylsulfonium p-toluene sulfonate
(b) cyclopropyl n-decyl phenylsulfonium p-toluene sulfonate
(c) cyclopropyl phenyl n-tetradecylsulfonium p-toluene sulfonate;
(d) cyclopropyl n-octadecyl phenylsulfonium p-toluene sulfonate; and
(e) cyclopropyl n-tetradecyl p-methoxyphenylsulfonium p-toluene sulfonate.

EXAMPLE 6

Capsules and tablets containing the ingredients indicated below may be prepared by conventional techniques and are useful in treating obesity in mammals at a dose of one capsule or tablet two to four times per day:

| Ingredient | Weight in Milligrams | | |
|---|---|---|---|
| | Tablet | Capsule | Capsule |
| Cyclopropyl n-propyl phenylsulfonium p-toluene sulfonate | 50 | 50 | 50 |
| Tragacanth | 10 | | |
| Lactose | 197.5 | 200 | |
| Corn Starch | 25 | | |
| Talcum | 15 | | |
| Magnesium Stearate | 2.5 | | |
| Corn oil | | | 200 |

What is claimed is:

1. A method of treating obesity in a mammal in need of such treatment, which comprises administering to said mammal an obesity treating effective amount of a compound of the formula:

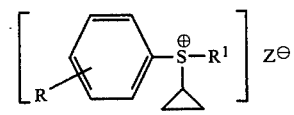

wherein
R is a hydrogen atom, alkyl having from 1 to 4 carbon atoms, alkoxy having from 1 to 4 carbon atoms, halo having an atomic weight of from about 19 to 35 or trifluoromethyl;
$R^1$ is alkyl having from 1 to 20 carbon atoms; and
Z is $BF_4$, $ClO_4$ or $SO_3R^2$;
wherein $R^2$ is methyl, phenyl, p-tolyl, or 2-naphthyl.

2. A pharmaceutical composition useful in treating obesity comprising in unit dosage form a pharmaceutically acceptable carrier and from 50 to 3,000 milligrams of a compound of the formula:

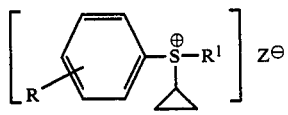

wherein
R is a hydrogen atom, alkyl having from 1 to 4 carbon atoms, alkoxy having from 1 to 4 carbon atoms, halo having an atomic weight of from about 19 to 35 or trifluoromethyl;
$R^1$ is alkyl having from 1 to 20 carbon atoms; and
Z is $BF_4$, $ClO_4$ or $SO_3R^2$;
wherein $R^2$ is methyl, phenyl, p-tolyl, or 2-naphthyl.

3. A method of claim 1 in which the daily dosage of compound is about 50 milligrams to about 3000 milligrams.

* * * * *